(12) United States Patent
Motoki (10) Patent No.: US 9,456,789 B2
(45) Date of Patent: Oct. 4, 2016

(54) OBJECT INFORMATION ACQUISITION APPARATUS

(71) Applicant: CANON KABUSHIKI KAISHA, Tokyo (JP)

(72) Inventor: Yohei Motoki, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 616 days.

(21) Appl. No.: 13/657,184

(22) Filed: Oct. 22, 2012

(65) Prior Publication Data

US 2013/0109952 A1    May 2, 2013

(30) Foreign Application Priority Data

Oct. 26, 2011 (JP) .................. 2011-235134

(51) Int. Cl.
*A61B 6/00* (2006.01)
*A61B 5/00* (2006.01)

(52) U.S. Cl.
CPC .............. *A61B 6/00* (2013.01); *A61B 5/0095* (2013.01)

(58) Field of Classification Search
None
See application file for complete search history.

(56) References Cited

U.S. PATENT DOCUMENTS

| | | | | | |
|---|---|---|---|---|---|
| 4,286,602 | A | * | 9/1981 | Guy | 600/476 |
| 5,007,428 | A | * | 4/1991 | Watmough | 600/440 |
| 5,231,464 | A | * | 7/1993 | Ichimura et al. | 356/477 |
| 5,293,873 | A | * | 3/1994 | Fang | 600/437 |
| 5,348,002 | A | * | 9/1994 | Caro | 600/310 |
| 5,713,356 | A | * | 2/1998 | Kruger | 600/407 |
| 5,722,407 | A | * | 3/1998 | Klingenbeck-Regn et al. | 600/368 |
| 5,999,836 | A | * | 12/1999 | Nelson et al. | 600/407 |
| 6,212,421 | B1 | * | 4/2001 | Vo-Dinh et al. | 600/407 |
| 6,668,187 | B1 | * | 12/2003 | Porath | 600/476 |
| 7,006,676 | B1 | * | 2/2006 | Zeylikovich et al. | 382/131 |
| 7,555,332 | B2 | * | 6/2009 | Rice et al. | 600/473 |
| 7,742,561 | B2 | * | 6/2010 | Ueki | 378/63 |
| 2001/0050769 | A1 | * | 12/2001 | Fujinaka | 356/121 |
| 2004/0032576 | A1 | * | 2/2004 | Kondo | 355/53 |

(Continued)

FOREIGN PATENT DOCUMENTS

| | | |
|---|---|---|
| JP | 2009-18153 A | 1/2009 |
| JP | 2011-92631 A | 5/2011 |

OTHER PUBLICATIONS

Manohar et al. "The Twente Photoacoustic Mammoscope: system overview and performance", Phys. Med. Biol. 50 (2005) 2543-2557.*

(Continued)

*Primary Examiner* — Don N. Ho
(74) *Attorney, Agent, or Firm* — Canon U.S.A., Inc. IP Division (57) ABSTRACT

An object information acquisition apparatus includes a holding member including a movable holding member configured to be movable in a direction of sandwiching an object, an irradiation member configured to irradiate the object with light from a light source through the holding member, an acoustic wave detection unit configured to receive an acoustic wave generated in the object by the light and to convert the acoustic wave into an electrical signal, a processing unit configured to acquire information in the object by using the electrical signal, a light diffusion member configured to be arranged on the movable holding member, and an imaging unit configured to capture an optical pattern formed when the light diffusion member is irradiated with the light, wherein the imaging unit is configured to be capable of adjusting a focus according to a movement of the movable holding member.

12 Claims, 6 Drawing Sheets

(56) References Cited

U.S. PATENT DOCUMENTS

| | | | |
|---|---|---|---|
| 2007/0043341 A1* | 2/2007 | Anderson et al. | 606/12 |
| 2007/0165202 A1* | 7/2007 | Koehler et al. | 355/67 |
| 2008/0031494 A1* | 2/2008 | Rice et al. | 382/110 |
| 2008/0306371 A1* | 12/2008 | Fukutani et al. | 600/407 |
| 2009/0005685 A1* | 1/2009 | Nagae et al. | 600/459 |
| 2009/0069674 A1* | 3/2009 | Masumura et al. | 600/425 |
| 2010/0087733 A1* | 4/2010 | Nakajima et al. | 600/437 |
| 2010/0094561 A1* | 4/2010 | Masumura | 702/19 |
| 2010/0208965 A1* | 8/2010 | Jiang et al. | 382/131 |

OTHER PUBLICATIONS

Manohar et al, "Photoacoustic mammography laboratory prototype: imaging of breast tissue phantoms", Journal of Biomedical Optics 9(6), 1172-1181 (Nov./Dec. 2004).*

* cited by examiner

FIG. 5

OBJECT INFORMATION ACQUISITION APPARATUS

BACKGROUND OF THE INVENTION

1. Field of the Invention

The present invention relates to an object information acquisition apparatus. In particular, the present invention relates to an object information acquisition apparatus that acquires acoustic waves generated by irradiating an object with light.

2. Description of the Related Art

Imaging techniques for irradiating an object such as a living body with light from a light source such as a laser and for imaging information in the living body resulting from the incident light have been discussed. Among such techniques is a photoacoustic imaging technique.

The photoacoustic imaging technique includes irradiating the living body with pulsed light emitted from the light source, receiving acoustic waves that are generated by body tissue absorbing the light propagated and diffused through the living body, and performing analysis processing on the received acoustic waves to visualize information in the living body, which is an object. The results are optical characteristic distributions in the living body, or an optical absorption coefficient distribution and an oxygen saturation distribution, in particular. Studies have been made to diagnose the object by using an image of the optical absorption coefficient distribution and such.

In photoacoustic imaging, an initial sound pressure $P0$ of the acoustic waves occurring from a light absorber in the object can be expressed by the following equation (1) (see Japanese Patent Application Laid-Open No. 2009-18153):

$$P0 = \Gamma \cdot \mu a \cdot \Phi \qquad (1)$$

where $\Gamma$ is a Grüneisen coefficient. The Grüneisen coefficient $\Gamma$ is a product of a coefficient of volumetric expansion $\beta$ and the square of a speed of sound c, divided by a specific heat at constant pressure CP. Given the object, $\Gamma$ is known to have a near constant value. $\mu a$ is an optical absorption coefficient of the light absorber and $\Phi$ is a fluence in a regional area.

A sound pressure P, which is the magnitude of the acoustic waves propagated through the object, is measured for temporal changes, and an initial sound pressure distribution is calculated from the measurements. The calculated initial sound pressure distribution is divided by the Grüneisen coefficient $\Gamma$ to determine a light energy absorption density distribution, which is the product of $\mu a$ and $\Phi$. As shown by equation (1), in order to determine the distribution of the optical absorption coefficient $\mu a$ from the distribution of the initial sound pressure $P0$, the distribution of the fluence $\Phi$ (light amount distribution) in the object needs to be determined.

The distribution of the fluence $\Phi$ can be calculated by using a relative light irradiation density distribution (hereinafter, also referred to as a "relative illuminance distribution") of light with which a surface is irradiated. The relative illuminance distribution is a relative light intensity distribution in a light irradiation area of the surface of the object. The relative illuminance distribution is determined by capturing an optical pattern that occurs on the object surface when the object surface is irradiated with the light. The relative illuminance distribution can be analyzed to calculate the light amount distribution in the object. Using the light amount distribution, the optical absorption distribution in the object can be determined from equation (1).

An apparatus using the photoacoustic imaging technique is intended to measure a living body as the object. More specifically, intended objects include diagnostic target regions such as a breast, fingers, hands, and feet of a human body or an animal. The apparatus generates image data on the optical absorption distribution in such target regions.

For measurement, a fixed target region is irradiated with light pulses to acquire acoustic waves from inside the target region. To determine the relative illuminance distribution of the light with which the surface is irradiated, the object may be sandwiched between two holding plates serving as a holding member, for example. The irradiation of the light pulses and the acquisition of the acoustic waves occurring in the object may be performed through the holding plates.

At least either one of the two holding plates may be configured to be movable in the direction of sandwiching the object, whereby the object-holding operation can be smoothly performed. An optical pattern of the light pulses on the holding plate can be captured to determine the relative illuminance distribution of the light with which the object surface is irradiated.

If the holding plate moves in the direction of sandwiching the object and the light emission position is fixed, the distance from the light emission position to the object changes with a change in the distance where the object is held. Since the total amount of light incident on the object varies with the distance from the emission position, the relative illuminance distribution occurring on the object surface changes. To obtain an accurate optical absorption distribution, the relative illuminance distribution occurring on the object surface needs to be measured according to the light emission position and the distance to the held object.

If an imaging unit for capturing the optical pattern, such as a camera, is fixed, the distance between the imaging unit and the object also changes. As a result, the imaging unit that captures an image of the object goes out of focus and fails to capture a clear optical pattern. The relative light irradiation densities occurring on the object are, therefore, not able to be measured with a high accuracy. Accordingly, the accurate optical characteristic distributions in the object, such as the optical absorption coefficient distribution, cannot be determined.

SUMMARY OF THE INVENTION

An example of the present invention is directed to capturing an optical pattern with a high accuracy to acquire an optical characteristic distribution in an object with a high accuracy even if a holding member holding the object moves.

According to an aspect of the present invention, an object information acquisition apparatus includes a holding member including a movable holding member configured to be movable in a direction of sandwiching an object, an irradiation member configured to irradiate the object with light from a light source through the holding member, an acoustic wave detection unit configured to receive an acoustic wave generated in the object by the light and to convert the acoustic wave into an electrical signal, a processing unit configured to acquire information in the object by using the electrical signal, a light diffusion member configured to be arranged on the movable holding member, and an imaging unit configured to capture an optical pattern formed when the light diffusion member is irradiated with the light, wherein the imaging unit is configured to be capable of adjusting a focus according to a movement of the movable holding member.

According to an exemplary embodiment of the present invention, the optical pattern can be captured with a high accuracy even if the holding member holding the object moves. The optical characteristic distribution in the object can thus be acquired with a high accuracy.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

As a rule, similar components will be designated by the same reference numerals. A description thereof will be omitted.

In an exemplary embodiment of the present invention, acoustic waves typically refer to ultrasonic waves and may include elastic waves called sound waves, ultrasonic waves, photoacoustic waves, and photo-ultrasonic waves. An object information acquisition apparatus according to the exemplary embodiment of the present invention includes a photoacoustic imaging apparatus that irradiates an object with light (electromagnetic waves including visible light and infrared rays) and receives acoustic waves generated in the object to acquire object information as image data.

The object information to be acquired refers to characteristic information that reflects an initial sound pressure distribution of the acoustic waves generated by the light irradiation, a light energy absorption density distribution derived from the initial sound pressure distribution, an absorption coefficient distribution, or a concentration distribution of a substance that constitutes a tissue. Examples of the concentration distribution of the substance include an oxygen saturation distribution and an oxidized or reduced hemoglobin concentration distribution.

Intended objects are living bodies. More specifically, diagnostic target regions such as a breast, fingers, hands, and feet of a human body or an animal are included. A light absorber in an object refers to a tissue that has a relatively high optical absorption coefficient in the object. Examples include blood vessels and malignant tumors containing a lot of new blood vessels.

Figure 1A:
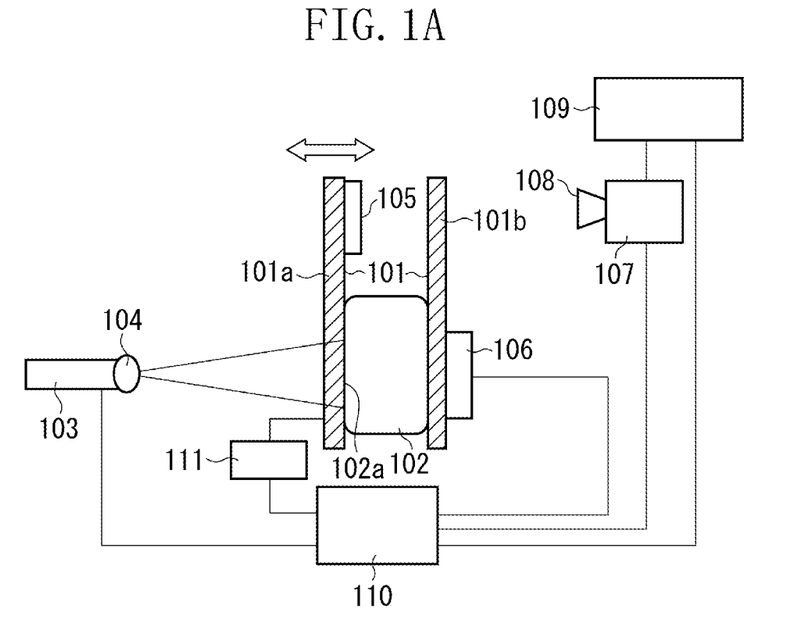
FIGS. 1A and 1B are schematic diagrams illustrating an example of a photoacoustic imaging apparatus according to a first exemplary embodiment.
Figure 1B:
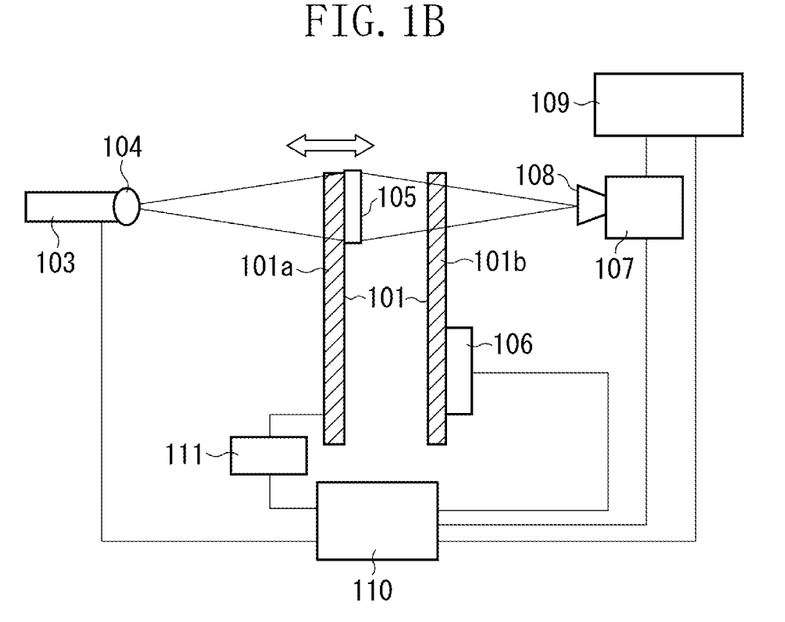

A first exemplary embodiment of the present invention will be described below with reference to FIGS. 1A and 1B to FIGS. 3A, 3B, and 3C. FIGS. 1A and 1B are schematic diagrams illustrating an example of the configuration of a photoacoustic imaging apparatus, which is the object information acquisition apparatus according to the present exemplary embodiment.

FIG. 1A is a schematic diagram illustrating a state where the photoacoustic imaging apparatus measures an object. The object 102 is held between a movable holding plate 101a and a fixed holding plate 101b of a holding member 101. The movable holding plate 101a moves in an object sandwiching direction to sandwich the object 102. The movable holding plate 101a corresponds to a movable holding member according to an exemplary embodiment of the present invention.

A light source 103 generates light (pulsed light) to irradiate the object 102 therewith through an optical unit 104, which is an irradiation member. When the object 102 is irradiated with the light, a light absorber (an object to be detected, such as a tumor) in the object absorbs light energy and generates acoustic waves. The generated acoustic waves propagate through the object to reach an acoustic wave probe 106, which is an acoustic wave detection unit, via the fixed holding plate 101b. The acoustic wave probe 106 receives the acoustic waves, converts the acoustic waves into an electrical signal, and outputs the electrical signal to an arithmetic processing unit 110 serving as a processing unit.

Using the input electrical signal, the arithmetic processing unit 110 acquires a characteristic distribution such as an optical absorption coefficient distribution in the form of photoacoustic image data.

FIG. 1B is a schematic diagram illustrating an example where the photoacoustic imaging apparatus according to the present exemplary embodiment measures a relative illuminance distribution. In the exemplary embodiment of the present invention, the relative illuminance distribution on the object surface is used to generate the photoacoustic image data.

The relative illuminance distribution refers to a relative light intensity distribution in a light irradiation area on a surface 102a of the object 102. An imaging camera 107 captures an optical pattern at the position where the object 102 is held, whereby the relative illuminance distribution occurring on the object surface is estimated.

Specifically, to measure the relative illuminance distribution, a light diffusion member 105 is arranged on the surface of the movable holding plate 101a, which the object 102 is arranged to contact. The optical unit 104, which is the irradiation member, irradiates the light diffusion member 105 with the light. The imaging camera 107 serving as an imaging unit captures the optical pattern (diffusion light pattern) occurring on the surface of the light diffusion member 105.

The imaging camera 107 includes an optical system 108 such as a lens. The arithmetic processing unit 110 performs analysis processing on the captured optical pattern to calculate the relative illuminance distribution.

In the present exemplary embodiment, the optical unit 104 (i.e., light emission position) is fixed. If the movable holding plate 101a is moved toward the fixed holding plate 101b, the distance from the light emission position to the movable holding plate 101a changes with a change in the distance where the object is held. Since the light diffusion member 105 is fixed to the movable holding plate 101a, the imaging camera 107 goes out of focus when capturing an optical pattern in an arbitrary position. The photoacoustic imaging apparatus according to the present exemplary embodiment then includes a focus adjustment mechanism 109 serving as an adjustment unit.

The focus adjustment mechanism 109 of the present exemplary embodiment mechanically moves the imaging camera 107 according to the movement of the light diffusion member 105. The focus adjustment mechanism 109 can adjust the focus of the imaging camera 107. The focus-adjusted imaging camera 107 thus captures a clear optical pattern.

The imaging camera 107 outputs the captured optical pattern to the arithmetic processing unit 110. The arithmetic processing unit 110 calculates the relative illuminance distribution. During the measurement of the relative illuminance distribution, the acoustic wave probe 106 is positioned not to disturb the imaging. For that purpose, the acoustic wave probe 106 is configured to be movable. Specifically, in the present exemplary embodiment, the acoustic wave probe 106 includes a scanning mechanism (not illustrated) for scanning along the surface of the fixed holding plate 101b. In the present exemplary embodiment, a distance measurement unit 111 measures the distance of the movement of the movable holding plate 101a and outputs the distance to the arithmetic processing unit 110. Then, the arithmetic processing unit 110 transmits a command to the focus adjustment mechanism 109.

The configuration of the photoacoustic imaging apparatus according to the present exemplary embodiment will be concretely described below.

The holding member 101 includes the fixed holding plate 101b serving as a fixed holding member and the movable holding plate 101a serving as a movable holding member. The holding member 101 is a holding unit for holding at least a part of the object 102 in a constant shape.

As illustrated in FIG. 1A, the object 102 is sandwiched from both sides. This can fix the position of the object 102 during measurement to reduce position changes due to body motions. In addition, sandwiching the object 102 can reduce (thin) the distance of the object 102 (the thickness in the light incident direction) so that the light efficiently reaches deep portions of the object 102. A member having high light transmittance can be used for the holding member on the side where the irradiation member is arranged.

On the other hand, a member having high acoustic consistency with the object 102 and the acoustic wave probe 106 can be used for the holding member on the side where the acoustic wave probe 106 is arranged. To improve the acoustic consistency, an acoustic adaptive material such as a gel may be interposed between the holding member 101 and the object 102. An irradiation member may also be arranged on the side of the fixed holding plate 101a of the holding member 101 so that the object 102 is irradiated with light from both sides. Both the holding members 101a and 101b may be configured to be movable.

The light source 103 includes at least one of coherent and incoherent pulsed light sources. To produce the photoacoustic effect, the light source 103 may have a pulse width less than or equal to several hundreds of nanoseconds. A range of 5 to 50 nsec is more desirable. For breast cancer measurement, the light source 103 emits a certain wavelength of light that is absorbed by a certain component (for example, hemoglobin) among the components constituting a living body.

Specifically, light emitted from the light source 103 can have a wavelength in the range of 500 to 1200 nm inclusive. The light source 103 can include a high-output laser. A light-emitting diode may be used instead of a laser. Various types of lasers including solid lasers, gas lasers, dye lasers, and semiconductor lasers may be used. Nd:YAG lasers and Ti:sapphire lasers may be used. The wavelength may be variable.

The optical unit 104 is an irradiation member for guiding the light from the light source 103 to the object 102. Examples include an optical fiber, a mirror for reflecting light, a half mirror for separating reference light and irradiation light, and a lens for condensing, magnifying, and/or deforming a light beam.

Such optical unit 104 may include members other than mirrors and lenses. Any member may be used as long as the object 102 can be irradiated with a light beam of desired shape emitted from the light source 103. It is useful to diffuse the light through a lens to spread over a certain extent of area. To irradiate a wide range of area with the light, the region of the object to be irradiated with the light can be movable over the object. Examples of the methods for moving the region of the object to be irradiated with the light include a method using a movable mirror and a method of moving a light-emitting end of an optical fiber.

The light diffusion member 105 can diffuse the light to eliminate areas where the irradiation energy density is locally high. The reason for the use of the light diffusion member 105 is that the light emitted from the optical unit 104 is so intense that the imaging camera 107 is not able to capture a favorable optical pattern if the imaging camera 107 directly captures the emitted light. In the exemplary embodiment of the present invention, the light diffusion member 105 is irradiated with the light and the imaging camera 107 captures the optical pattern formed on the surface of the light diffusion member 105.

The light diffusion member 105 is desirably a diffusion plate such as frosted glass, or a diffusion sheet such as a thin urethane sheet containing titanium oxide. The light diffusion member 105 desirably has isotropic circular diffusion with uniform diffusion angles sufficiently greater than the angle of view of the lens of the imaging camera 107.

For example, given an angle of view of 20°, the light diffusion member 105 desirably has a diffusion angle greater than or equal to 60° so that diffused light will not vary in intensity within the angle range of ±10°. The light diffusion member 105 may be detachably attached to the holding member 101, and it may be integrated with the holding member 101. The light diffusion member 105 can have a thickness of around 0.1 to 1.0 mm.

The acoustic wave probe 106 is an acoustic wave detection unit, which includes one or more elements for receiving and converting acoustic waves into an electrical signal. Any conversion element may be used as long as acoustic waves can be received and converted into an electrical signal. Examples include a transducer using a piezoelectric effect, a transducer using light resonance, and a transducer using a change in capacitance. A plurality of such elements may be arranged in one dimension or two dimensions, whereby acoustic waves can be simultaneously received in a plurality of places for reduced reception time.

A single element may be moved to acquire signals similar to those of a plurality of elements in a two-dimensional or one-dimensional arrangement. In FIGS. 1A and 1B, the acoustic wave probe 106 is arranged on the side of the fixed holding plate 101b. The acoustic wave probe 106 may be arranged on the side of the movable holding plate 101a, or on both sides.

The imaging camera 107 is an imaging unit, which includes one or more elements for detecting and converting light into an electrical signal. The imaging camera 107 includes a photomultiplier tube (s) or photo diode (s). Any element may be used as long as light can be detected and converted into an electrical signal.

A plurality of light detecting elements may be arranged in one dimension or two dimensions, whereby light can be simultaneously detected in a plurality of places. The elements need to be sensitive to the wavelength range of the irradiation light. The imaging camera 107 includes the optical system 108, including a neutral density (ND) filter and a lens. The lens has a focal length such that the imaging camera 107 can capture the entire optical pattern of the irradiation light diffused on the light diffusion member 105.

The focus adjustment mechanism 109 is an adjustment unit for adjusting the focus of the imaging camera 107 according to the movement of the movable holding member 101a. In the present exemplary embodiment, the focus adjustment mechanism 109 includes a feeding mechanism and a linear motion mechanism for moving the imaging camera 107 to follow the light diffusion member 105. Examples include a linear guide and a ball screw. The focus adjustment mechanism 109 may have any configuration as long as it adjusts the focus according to the movement of the light diffusion member 105 (i.e., moves the focus to follow the movement of the light diffusion member 105).

Figure 3A:
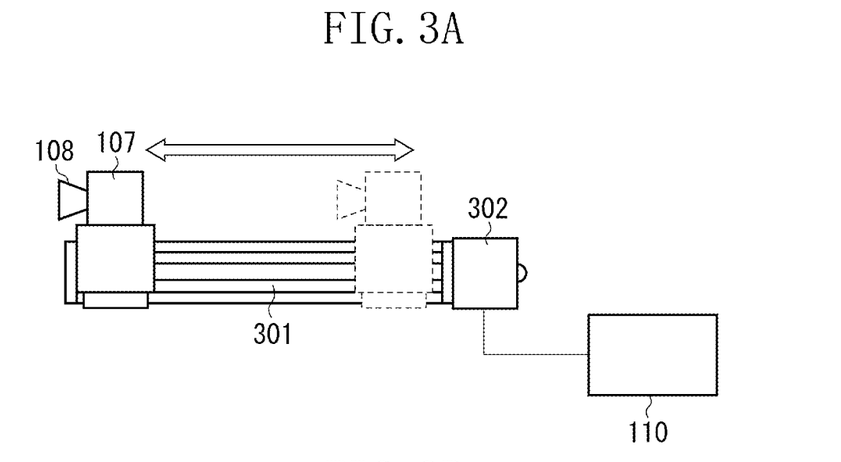
FIGS. 3A, 3B, and 3C are schematic diagrams illustrating examples of a focus adjustment unit of an imaging unit according to the first exemplary embodiment.
Figure 3B:
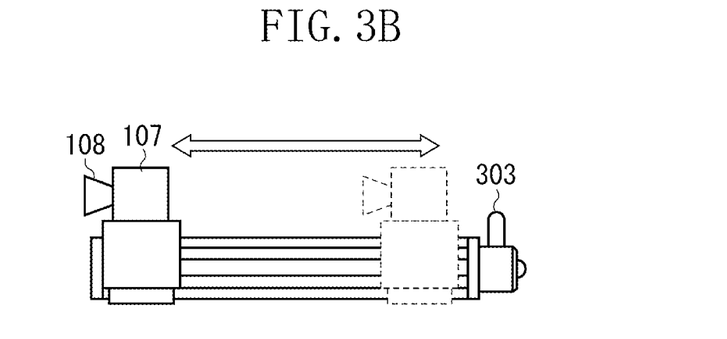
Figure 3C:
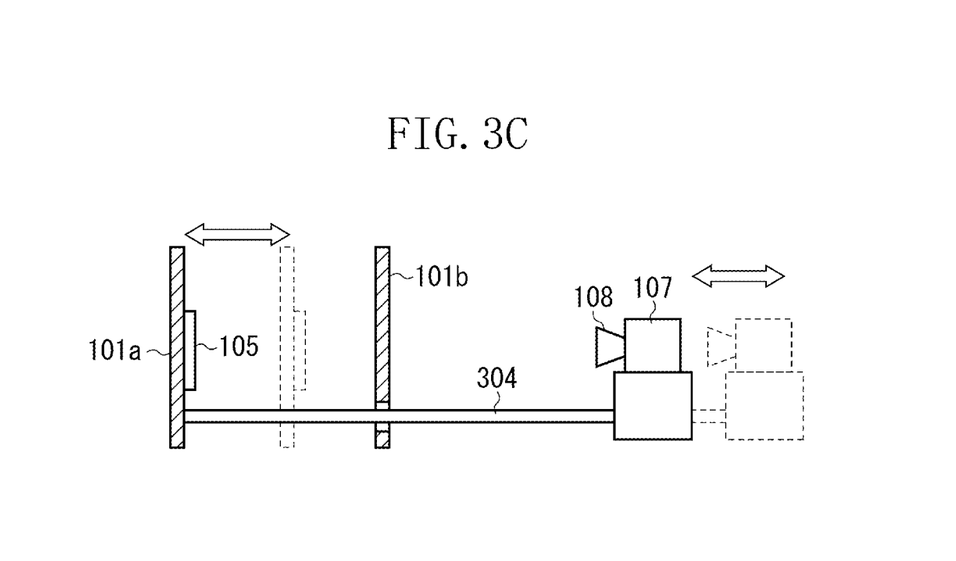

FIGS. 3A, 3B, and 3C illustrate examples of the imaging camera 107 and the focus adjusting mechanism 109.

FIG. 3A illustrates an example where the focus adjustment mechanism 109 includes a motor 302 and linear guides 301. Examples of the motor 302 include a direct-current (DC) motor, a stepping motor, and an electromagnetic motor. The distance measurement unit 111 (see FIGS. 1A and 1B) may measure the distance of the movement of the movable holding plate 101a by using a feeding mechanism and a linear motion mechanism. The distance measurement unit 111 may output the distance to the arithmetic processing unit 110, and the arithmetic processing unit 110 may transmit a command to the motor 302.

As illustrated in FIG. 3B, a handle 303 may be used to manually move the imaging camera 107 to follow the light diffusion member 105. In such a case, the distance measurement unit 111 may measure the distance of the movement of the light diffusion member 105 and present the distance to a user. The user may directly move the imaging camera 107 along the guides without using the handle.

The focus adjustment mechanism 109 is not limited to a feeding mechanism or a linear motion mechanism. As illustrated in FIG. 3C, the light diffusion member 105 and the imaging camera 107 may be connected by a shaft 304 in such a manner that the light diffusion member 105 and the imaging camera 107 are mechanically fixed at a constant distance.

The arithmetic processing unit 110 is a processing unit that calculates the relative illuminance distribution, generates image data including an optical absorption coefficient distribution, and transmits a command to the focus adjustment mechanism 109. A workstation is typically used as the arithmetic processing unit 110. The arithmetic processing unit 110 performs processing for calculating the relative illuminance distribution and feeding back the result to the irradiation light according to previously-programmed software.

The arithmetic processing unit 110 may perform noise reduction processing on the electrical signal acquired from the acoustic wave probe 106. Aside from the movement control of the imaging camera 107, the arithmetic processing unit 110 may also perform overall processing for operating the photoacoustic imaging apparatus. Examples include the control of the scanning mechanisms of the acoustic wave probe 106 and the optical unit 104.

Figure 2:
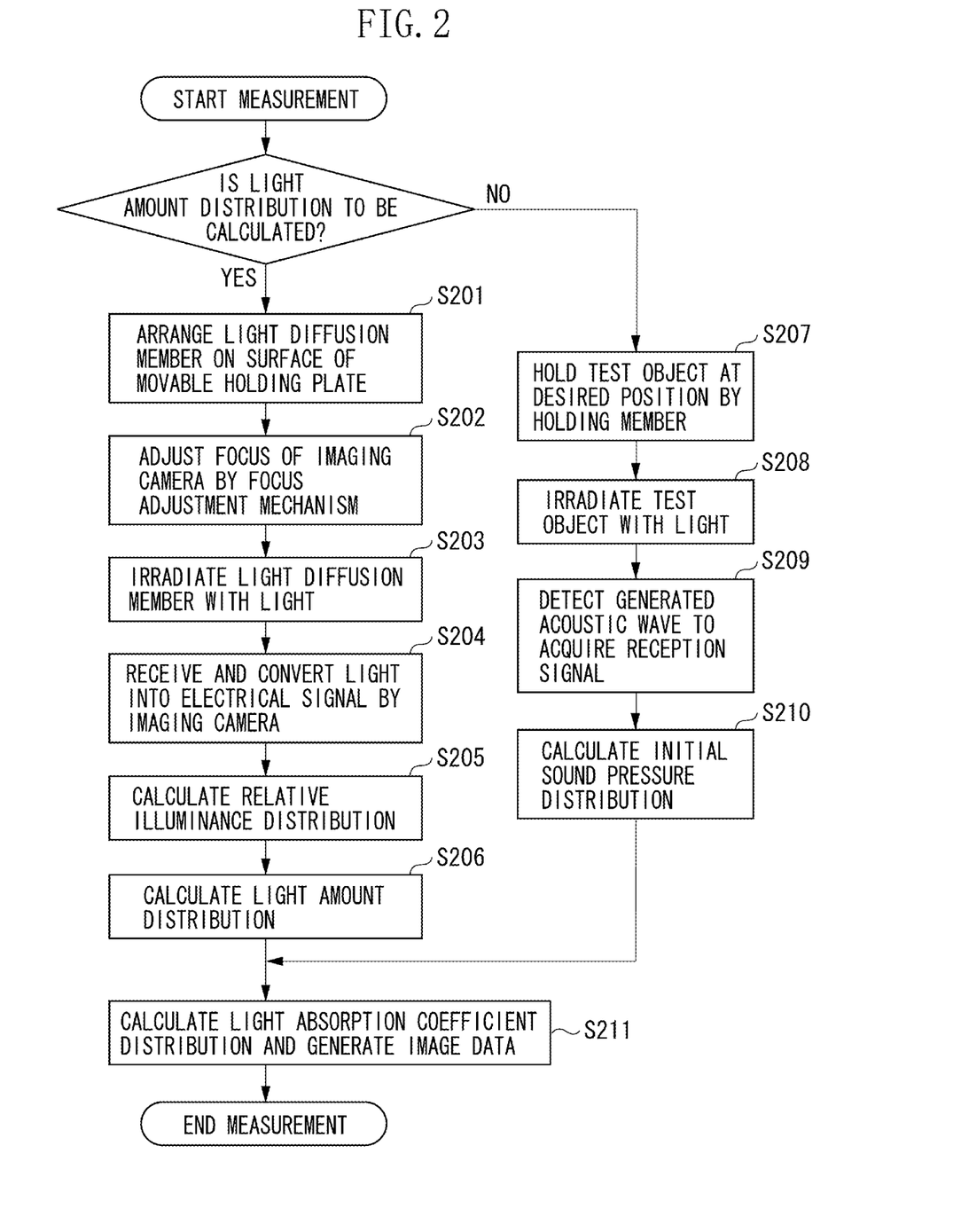
FIG. 2 is a flowchart illustrating a measurement procedure according to the first exemplary embodiment.

A measurement procedure of the photoacoustic imaging apparatus according to the present exemplary embodiment will be described with reference to a measurement flowchart illustrated in FIG. 2.

The present procedure deals with an example of acquiring the optical absorption coefficient distribution as the characteristic information in the object 102. According to the measurement procedure of the present exemplary embodiment, several patterns of light amount distribution for different holding plate distances (for example, several patterns at distances changed in units of several millimeters) are acquired to create a table in advance before the acquisition of the characteristic information about the object 102. A sound pressure distribution is then acquired with the object 102 held with a distance L. Subsequently, the data on the light amount distribution at the previously-measured position of the distance L (or the data on the light amount distribution closest to the distance L) is read.

Note that the exemplary embodiment of the present invention is not limited to such measurement procedure. For example, the light amount distribution may be acquired after the object 102 is held by the holding member 101 and before the object 102 is irradiated with the light to acquire the characteristic information. In this case, the light amount distribution can be acquired in the same state as where the object 102 is actually held. The characteristic information can thus be acquired more accurately.

An example according to the former measurement procedure will be described below. Initially, the procedure up to the acquisition of the light amount distribution will be described.

In step S201, as illustrated in FIG. 1B, the user arranges the light diffusion member 105 on the surface of the movable holding plate 101a to be irradiated with the irradiation light. The object 102 is not placed in the holding member 101. In step S202, the user moves the movable holding plate 101a to a desired position, and the focus adjustment mechanism 109 moves the capturing imaging camera 107 by the same distance to follow the movable holding plate 101a.

In step S203, the light diffusion member 105 is irradiated with the light emitted from the light source 103 through the optical unit 104. Here, the acoustic wave probe 106 is positioned not to interfere with the position of the light diffusion member 105 and the position of the imaging camera 107.

The irradiation light with which the light diffusion member 105 is irradiated is diffused on the light diffusion member 105. In step S204, the imaging camera 107 captures the resulting optical pattern. The light detected by the light detection element(s) in the imaging camera 107 is converted into a first electrical signal (imaging signal).

In step S205, the arithmetic processing unit 110 receives the first electrical signal, and calculates the relative illuminance distribution at the position of the light diffusion member 105 by using the first electrical signal. Specifically, the arithmetic processing unit 110 calculates the relative illuminance distribution on the object surface based on the optical pattern captured by the imaging camera 107 and the previously-measured size of the object to be captured (here, the light diffusion member 105) per pixel. The arithmetic processing unit 110 thereby estimates the relative illuminance distribution on the object surface when the object 102 is irradiated with the irradiation light from the light source 103.

In step S206, the arithmetic processing unit 110 calculates the light amount distribution in the object 102 based on the calculated relative illuminance distribution. Specifically, the arithmetic processing unit 110 calculates the light amount distribution by using an optical diffusion equation, a transport equation, or a Monte Carlo light propagation simulation, with a virtual light source having the same relative illuminance distribution as the foregoing relative illuminance distribution on the surface of the object in a calculation space.

Now, the procedure up to the calculation of the sound pressure distribution occurring in the object 102 will be described.

In step S207, as illustrated in FIG. 1A, the object 102 is held at a desired position by the holding member 101. The user places the acoustic wave probe 106 in a position opposed to where the object 102 is irradiated with the light. In step S208, the object 102 is irradiated with the light emitted from the optical unit 104 through the movable holding plate 101a.

The light absorbers in the object 102 absorb the light energy of the irradiation light and generate acoustic waves. In step S209, the acoustic wave probe 106 receives and converts the acoustic waves into a second electrical signal (reception signal). In step S210, the arithmetic processing unit 110 receives the second electrical signal, and calculates the initial sound pressure distribution by using the second electrical signal.

In step S211, the arithmetic processing unit 110 calculates the optical absorption coefficient distribution by using the initial sound pressure distribution calculated in step S210 and the light amount distribution calculated in step S206. Specifically, the arithmetic processing unit 110 calculates the optical absorption coefficient distribution by dividing the initial sound pressure distribution by the light amount distribution according to equation (1). Finally, the arithmetic processing unit 110 generates the optical absorption coefficient distribution calculated in step S211 as image data.

As described above, in the present exemplary embodiment, the light diffusion member 105 is used to capture an optical pattern with focus adjustment. This enables precise estimation of the relative illuminance distribution, whereby the characteristic information in the object 102 can be determined with a high accuracy.

In the first exemplary embodiment, the focus of the imaging camera 107 is adjusted by moving the imaging camera 107 to follow the movement of the light diffusion member 105. In a second exemplary embodiment, a focus function is used to adjust the focus without moving the imaging camera 107.

Figure 4A:
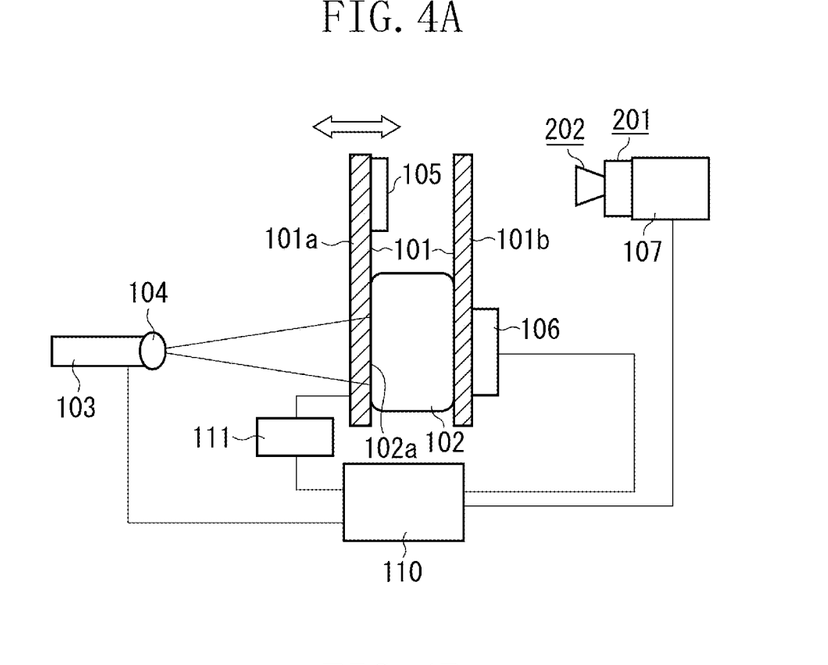
FIGS. 4A and 4B are schematic diagrams illustrating an example of the photoacoustic imaging apparatus according to a second exemplary embodiment.
Figure 4B:
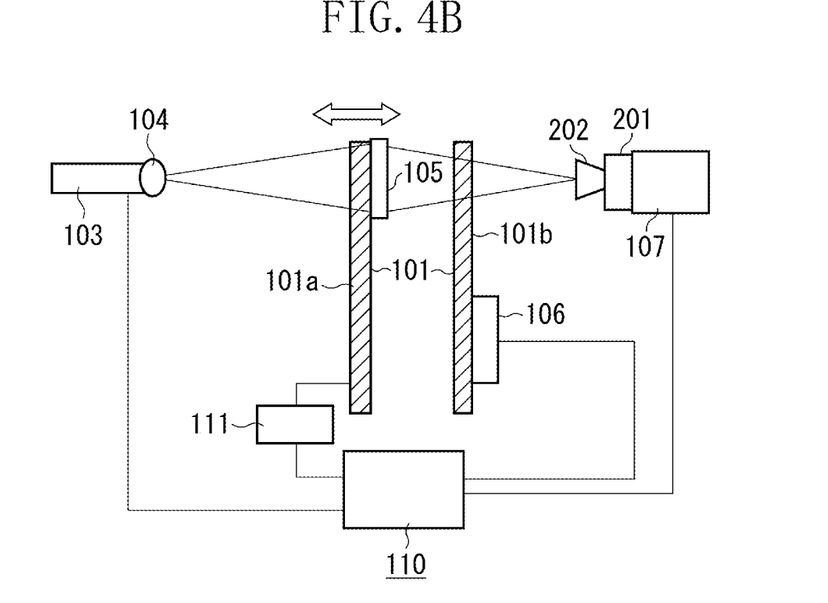

FIGS. 4A and 4B are schematic diagrams illustrating an example of the configuration of a photoacoustic imaging apparatus, which is the object information acquisition apparatus according to the second exemplary embodiment. The photoacoustic imaging apparatus according to the present exemplary embodiment has a configuration similar to that of the first exemplary embodiment except the imaging camera and the focus adjustment mechanism. Description of the parts similar to those of the first exemplary embodiment will be omitted.

FIG. 4A is a schematic diagram illustrating the state where the photoacoustic imaging apparatus measures the object 102. FIG. 4B is a schematic diagram illustrating an example where the photoacoustic imaging apparatus according to the present exemplary embodiment measures a relative illuminance distribution.

In the present exemplary embodiment, the imaging camera 107 serving as an imaging unit includes a focus adjustment mechanism 201 and an optical system 202. The imaging camera 107 can focus on an optical pattern occurring on the light diffusion member 105 at an arbitrary distance from the imaging camera 107 by adjusting the optical system 202, such as a lens, by the focus adjustment mechanism 201 without moving the position of the imaging camera 107 itself. The imaging camera 107 can thus capture a clear optical pattern.

Figure 5:
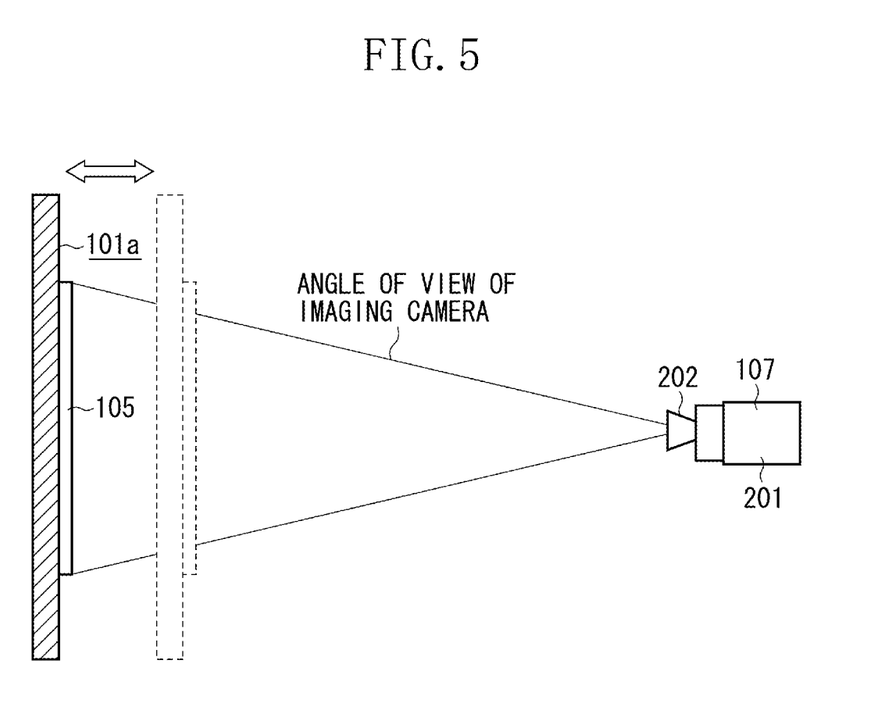
FIG. 5 is a schematic diagram illustrating the relationship between the imaging unit and a light diffusion member according to the second exemplary embodiment.

FIG. 5 illustrates the relationship between the angle of view of the imaging camera 107 and the position of the light diffusion member 105.

The broken lines indicate the position to which the light diffusion member 105 and the movable holding plate 101a move. Depending on the lens configuration of the imaging camera 107, the angle of view with which the imaging camera 107 can capture an image changes with the movement of the light diffusion member 105. Since the area of the light diffusion member 105 that can be imaged by the imaging camera 107 changes, the resulting relative illuminance distribution also varies with the position of the light diffusion member 105.

The arithmetic processing unit 110 may determine the relative illuminance distribution by performing correction (including image correction) of the imaging signal to correct the difference in the angle of view. For example, the arithmetic processing unit 110 may perform the correction according to the position of the light diffusion member 105 acquired by the distance measurement unit 111 with reference to the angle of view at which the entire light diffusion member 105 can be imaged.

The configuration of the imaging camera 107 will be concretely described.

The optical system 202 of the imaging camera 107 includes an ND filter and a lens. In most cases, the lens is desirably a zoom lens or a variable focus lens. As to the ND filter, any ND filter can be used as far as the imaging camera 107 can capture the entire optical pattern of the irradiation light diffused on the light diffusion member 105.

In most cases, the focus adjustment mechanism 201 is not limited to either manual focusing or auto focusing, whereas the optical system 202 is desirably adjusted automatically (by auto focusing). Both active type and passive type of auto focusing may be used. An ultrasonic motor, a stepping motor, or a DC motor may be mainly used as an auto-focusing drive unit. Such drive units provide the same effects as long as the optical system 202 can be moved back and forth.

For manual focusing, any method may be used as long as the imaging camera 107 properly focuses. Examples include a single-lens method, a twin-lens method, a range finder method, and manual focusing. For example, according to the range finder method, the focus adjustment mechanism 201 includes a measurement unit for measuring the amount of extension of the lens and an optical range finder. By interlocking such components, the user can adjust the focus based on split images or overlapping double images.

Now, a measurement procedure according to the present exemplary embodiment will be described in detail.

Figure 6:
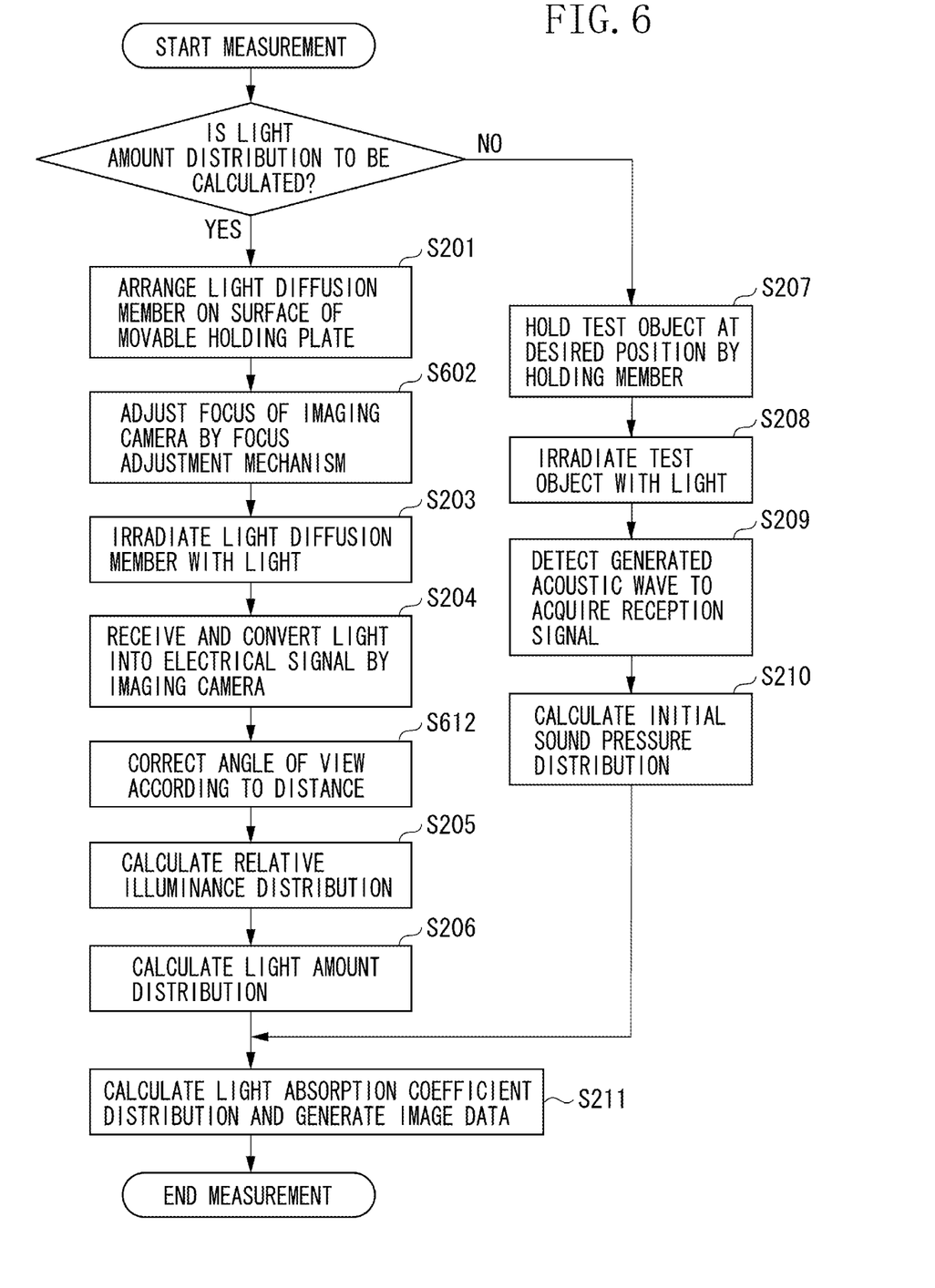
FIG. 6 is a flowchart illustrating the measurement procedure according to the second exemplary embodiment.

FIG. 6 is a flowchart for measurement when using the photoacoustic imaging apparatus according to the present exemplary embodiment. The procedure of the present exemplary embodiment is similar to that of the first exemplary embodiment (FIG. 2) except that a step concerning focus adjustment (step S602) and the correction of the angle of view (S612) are needed. A redundant description will be omitted.

In step S201, the user moves the movable holding plate 101a having the light diffusion member 105 to a desired position. In step S602, the distance measurement unit 111 measures the distance, and the arithmetic processing unit 110 commands and drives the focus adjustment mechanism 201 to move the lens and bring the imaging camera 107 into focus. Here, the user may manually operate the focus adjustment mechanism 201 for focus adjustment.

The light diffusion member 105 is irradiated with the irradiation light, which is diffused on the light diffusion member 105. The imaging camera 107 receives the optical pattern through the optical system 202, and converts the optical pattern into the first electrical signal (imaging signal). The arithmetic processing unit 110 receives the first electrical signal.

In step S612, the arithmetic processing unit 110 corrects the first electrical signal to correct the angle of view by using angle-of-view information of the imaging camera 107 according to the position of the light diffusion member 105. Here, the arithmetic processing unit 110 performs processing to correct the angle of view with respect to a certain position of the light diffusion member 105. In step S205, the arithmetic processing unit 110 calculates the relative illuminance distribution on the light diffusion member 105.

Such implementation of the focus adjustment mechanism 201 on the imaging camera 107 allows a compact configuration as compared to the configuration of mechanically moving the imaging camera 107.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2011-235134 filed Oct. 26, 2011, which is hereby incorporated by reference herein in its entirety.

What is claimed is:

1. An object information acquisition apparatus comprising:
    a holding member configured to hold an object;
    an irradiation member configured to irradiate the object with light from a light source through the holding member;
    an acoustic wave detection unit configured to receive an acoustic wave generated in the object by the light and to convert the acoustic wave into an electrical signal;
    a processing unit configured to acquire information in the object by using the electrical signal from the acoustic wave detection unit;
    a light diffusion member configured to be arranged on the holding member; and
    an imaging unit configured to capture an optical pattern formed when the light diffusion member is irradiated with the light,
    wherein a light emission position of the irradiation member and the light diffusion members are movable relative to each other by moving the holding member, and a distance between the light emission position of the irradiation member and the light diffusion member is changed by relative movement of the light emission position of the irradiation member and the light diffusion member, and
    wherein the imaging unit is configured to be capable of adjusting a focus according to the distance between the light emission position of the irradiation member and the light diffusion member by keeping a distance between the imaging unit and the light diffusion member constant.

2. The object information acquisition apparatus according to claim 1, further comprising an adjustment unit configured to mechanically move the imaging unit,
    wherein the adjustment unit is configured to move the imaging unit to adjust the focus according to the movement of the holding member.

3. The object information acquisition apparatus according to claim 1, wherein the holding member and the imaging unit are configured to be mechanically fixed at a constant distance.

4. The object information acquisition apparatus according to claim 1, wherein the processing unit is configured to acquire a relative illuminance distribution of the light with which the object is irradiated, by using an imaging signal output from the imaging unit.

5. The object information acquisition apparatus according to claim 1, wherein the holding member is a pair of holding members capable of holding the object therebetween.

6. The object information acquisition apparatus according to claim 5,
    wherein the pair of holding members includes a first holding member and a second holding member,
    wherein at least the first holding member is movable, and the holding member and the light emission position of the irradiation member are moved relative to each other by movement of the first holding member.

7. The object information acquisition apparatus according to claim 6, wherein the first holding member is configured to be movable in a direction of sandwiching the object.

8. The object information acquisition apparatus according to claim 2, wherein the adjustment unit is configured to move the imaging unit so that a relative position of the holding member and the imaging unit before the movement of the holding member is not changed after the movement of the holding member.

9. The object information acquisition apparatus according to claim 4,
    wherein a distance between the imaging unit and the light diffusion member is changed by the relative movement of the light emission position of the irradiation member and the light diffusion member, and
    wherein the processing unit is configured to compare a distance between the imaging unit and the light diffusion member when an optical pattern is captured at a reference angle of view with a distance between the imaging unit and the light diffusion member when a first optical pattern is captured at the reference angle of view and correct an imaging signal of the first optical pattern and acquire, based on the corrected imaging signal of the first optical pattern, a relative illuminance distribution when the first optical pattern is captured.

10. The object information acquisition apparatus according to claim 9, further comprising: a distance measurement unit configured to measure the distance between the imaging unit and the light diffusion member.

11. An object information acquisition apparatus comprising:
- a holding member including a movable holding member configured to be movable in a direction of sandwiching an object;
- an irradiation member configured to irradiate the object with light from a light source through the holding member;
- an acoustic wave detection unit configured to receive an acoustic wave generated in the object by the light and to convert the acoustic wave into an electrical signal;
- a processing unit configured to acquire information in the object by using the electrical signal;
- a light diffusion member configured to be arranged on the movable holding member; and
- an imaging unit configured to capture an optical pattern formed when the light diffusion member is irradiated with the light,
- wherein a distance between a light emission position of the irradiation member and the light diffusion member is changed by movement of the movable holding member,
- wherein the imaging unit is configured to be capable of adjusting a focus according to the distance between the light emission position of the irradiation member and the light diffusion member,
- wherein a distance between the imaging unit and the light diffusion member is changed by relative movement of the light emission position of the irradiation member and the light diffusion member, and
- wherein the processing unit is configured to compare a distance between the imaging unit and the light diffusion member when the optical pattern is captured at a reference angle of view with a distance between the imaging unit and the light diffusion member when a first optical pattern is captured at the reference angle of view and correct an imaging signal of the first optical pattern to correct the difference in the angle of view and acquire, based on the corrected imaging signal of the first optical pattern, a relative illuminance distribution when the first optical pattern is captured.

12. The object information acquisition apparatus according to claim 11, wherein the imaging unit is configured so that the focus is adjusted by moving an optical system included in the imaging unit, and
- wherein the processing unit is configured to correct an imaging signal output from the imaging unit to correct an angle of view of the imaging unit based on a relative position of the light diffusion member and the imaging unit.

* * * * *